United States Patent
Cavecchi et al.

(10) Patent No.: US 10,786,450 B2
(45) Date of Patent: *Sep. 29, 2020

(54) PROCESS FOR PREPARING A DRY POWDER FORMULATION COMPRISING AN ANTICHOLINERGIC, A CORTICOSTEROID AND A BETA-ADRENERGIC

(71) Applicant: CHIESI FARMACEUTICI S.p.A., Parma (IT)

(72) Inventors: Alessandro Cavecchi, Parma (IT); Cristiana Merusi, Parma (IT); Fausto Pivetti, Parma (IT); Francesca Schiaretti, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,146

(22) Filed: May 9, 2018

(65) Prior Publication Data

US 2018/0325816 A1 Nov. 15, 2018

(30) Foreign Application Priority Data

May 11, 2017 (EP) .................................... 17170657

(51) Int. Cl.

| | | |
|---|---|---|
| *A61K 9/00* | (2006.01) | |
| *A61K 31/40* | (2006.01) | |
| *A61K 9/14* | (2006.01) | |
| *A61K 31/167* | (2006.01) | |
| *A61K 47/12* | (2006.01) | |
| *A61K 47/14* | (2017.01) | |
| *A61K 31/573* | (2006.01) | |
| *A61P 11/06* | (2006.01) | |
| *A61P 11/08* | (2006.01) | |
| *A61K 47/26* | (2006.01) | |
| *A61K 31/4704* | (2006.01) | |
| *A61K 45/06* | (2006.01) | |
| *A61K 31/137* | (2006.01) | |
| *A61K 31/58* | (2006.01) | |
| *A61K 31/56* | (2006.01) | |
| *A61K 31/138* | (2006.01) | |

(52) U.S. Cl.
CPC ............ *A61K 9/0075* (2013.01); *A61K 9/145* (2013.01); *A61K 31/137* (2013.01); *A61K 31/138* (2013.01); *A61K 31/167* (2013.01); *A61K 31/40* (2013.01); *A61K 31/4704* (2013.01); *A61K 31/56* (2013.01); *A61K 31/573* (2013.01); *A61K 31/58* (2013.01); *A61K 45/06* (2013.01); *A61K 47/14* (2013.01); *A61K 47/26* (2013.01); *A61P 11/06* (2018.01); *A61P 11/08* (2018.01); *A61K 2300/00* (2013.01)

(58) Field of Classification Search
CPC ...... A61K 9/0075; A61K 31/40; A61K 9/145; A61K 31/167; A61K 31/573; A61K 45/06
See application file for complete search history.

(56) References Cited

U.S. PATENT DOCUMENTS

| | | | | |
|---|---|---|---|---|
| 9,808,422 | B2 * | 11/2017 | Pasquali | ............... A61K 31/167 |
| 10,028,964 | B2 * | 7/2018 | Monari | .................... A61K 9/14 |
| 10,086,004 | B2 * | 10/2018 | Cafiero | ................ A61K 9/0075 |
| 10,350,164 | B2 * | 7/2019 | Cavecchi | ............. A61K 31/573 |
| 2012/0308613 | A1 * | 12/2012 | Staniforth | ............ A61K 9/0075 |
| | | | | 424/400 |
| 2015/0017248 | A1 * | 1/2015 | Pasquali | ............... A61K 31/167 |
| | | | | 424/490 |
| 2015/0164915 | A1 * | 6/2015 | Monari | .................... A61K 9/14 |
| | | | | 128/203.15 |
| 2018/0360849 | A1 * | 12/2018 | Cafiero | ................ A61K 9/0075 |

FOREIGN PATENT DOCUMENTS

| | | |
|---|---|---|
| WO | 01/78693 | 10/2001 |
| WO | 2011/076843 | 6/2011 |
| WO | 2015/004243 | 1/2015 |
| WO | 2017/085004 | 5/2017 |
| WO | 2017/085007 | 5/2017 |

OTHER PUBLICATIONS

European Search Report in Application No. 17170657.5 dated Sep. 14, 2017, 8 pages.
International Search Report and Written Opinion dated Jul. 10, 2018 in PCT/EP2018/061953.

* cited by examiner

*Primary Examiner* — Mina Haghighatian
(74) *Attorney, Agent, or Firm* — Oblon, McClelland, Maier & Neustadt, L.L.P.

(57) ABSTRACT

A process for preparing a dry powder formulation for inhalation comprising a combination of an anti-cholinergic, a long-acting beta$_2$-adrenoceptor agonist, and a corticosteroid is provided.

16 Claims, No Drawings

PROCESS FOR PREPARING A DRY POWDER FORMULATION COMPRISING AN ANTICHOLINERGIC, A CORTICOSTEROID AND A BETA-ADRENERGIC

CROSS REFERENCES TO RELATED APPLICATIONS

This application claims priority to European Patent Application No. 17170657.5 filed on May 11, 2017, which is incorporated herein by reference in its entirety.

BACKGROUND OF THE INVENTION

Field of the Invention

The present invention relates to powder formulations for administration by inhalation by means of a dry powder inhaler. In particular, the present invention relates to a process for preparing a dry powder formulation comprising a combination of an anticholinergic, a beta$_2$-adrenoceptor agonist, and an inhaled corticosteroid.

Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung diseases include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aim of COPD management includes not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing, and in particular, combination therapies, with a view to their complementary modes of action enabling multiple components of the disease to be addressed. Evidence from recent clinical trials indicates that triple therapy, combining an anticholinergic with an inhaled corticosteroid, and a long-acting $\beta_2$-adrenoceptor agonist, may provide clinical benefits additional to those associated with each treatment alone in patients with more severe COPD.

Currently, there are several recommended classes of therapy for COPD, of which bronchodilators such as $\beta_2$-agonists and anticholinergics are the mainstay of symptom management in mild and moderate diseases, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicates that triple therapy, combining an anticholinergic with a long-acting $\beta_2$-agonist (LABA), and an ICS, may provide clinical benefits additional to those associated with each treatment alone in patients with moderate to severe forms of respiratory diseases, particular moderate to severe COPD.

An interesting triple combination, presently under investigation, includes:

(1) formoterol, particularly its fumarate salt (hereinafter indicated as FF), a long acting beta-2 adrenergic receptor agonist, currently used clinically in the treatment of asthma, COPD and related disorders;

(2) glycopyrronium bromide, an anticholinergic (antimuscarinic) recently approved for the maintenance treatment of COPD; and (3) beclometasone dipropionate (BDP) a potent anti-inflammatory corticosteroid, available under a wide number of brands for the prophylaxis and/or treatment of asthma and other respiratory disorders.

The solution formulation for administration by pressurized metered dose inhalers (pMDI) is disclosed in WO 2011/076843, which is incorporated herein by reference in its entirety.

Said formulation provides a high lung deposition and uniform distribution throughout the bronchial tree, and is characterized by the fact that is capable of delivering a high fraction of particles having a diameter equal or less than 2.0 micron for all the three active ingredients (hereinafter defined as extrafine fraction).

The major advantage of said formulation is related to the improved penetration into the bronchiole-alveolar distal part of the respiratory tree wherein inflammation is known to play a role in spontaneous exacerbations of asthma symptoms and wherein it is known that the density of the beta-2 adrenergic receptors is particularly high.

However, despite their popularity, pMDI formulations may have some disadvantages in particular in elderly and pediatric patients, mostly due to their difficulty to synchronize actuation from the device with inspiration.

Dry powder inhalers (DPIs) constitute a valid alternative to MDIs for the administration of drugs to airways.

Typically, drugs intended for inhalation as dry powders should be used in the form of micronized particles.

For example, powder formulations for inhalation by Dry Powder Inhalers (DPIs) containing all said three active ingredients in a micronized form are disclosed in WO 2015/004243, which is incorporated herein by reference in its entirety. Said formulation takes advantage of the technology platform disclosed in WO 01/78693, which is incorporated herein by reference in its entirety, entailing the use of carrier constituted of a fraction of coarse excipient particles and a fraction made of fine excipient particles and magnesium stearate. In the specification, possible processes for preparing micronized glycopyrronium bromide are described, but no preference is given.

On the other hand, similarly to other anti-muscarinic agents, glycopyrronium salts may face significant stability problems, especially immediately following conventional micronization processes by milling.

In fact, glycopyrronium bromide, once micronized, has a strong tendency to aggregate and/or agglomerate, which severely hinders downstream drug processing, particularly the preparation of dry powder formulations for administration by inhalation capable of delivering a good respirable fraction.

SUMMARY OF THE INVENTION

Accordingly, it is one object of the present invention to provide novel processes for preparing a powder formulation suitable to administer glycopyrronium bromide in combination with a LABA and an ICS overcoming the problems indicated above.

This and other objects, which will become apparent during the following detailed description, have been achieved by the inventors' discovery of the process described below.

Thus, the present invention provides a process for preparing a powder formulation for inhalation for use in a dry powder inhaler, said powder comprising:

(A) a carrier comprising:
(a) 80 to 95 percent by weight, based on the total weight of said carrier, of coarse particles of a physiologically acceptable excipient having a mass median particle size of at least 175 micron; and
(b) 19.6 to 4.9 percent by weight, based on the total weight of said carrier, of micronized particles of a physiologically acceptable excipient, and 0.1 to 0.4 percent by weight, based on the total weight of said carrier, of a salt of a fatty acid; and
(B) micronized particles of glycopyrronium bromide, a long-acting $\beta_2$-agonist (LABA) and an inhaled corticosteroid (ICS), as active ingredients, said process comprising:

(i) preparing by co-milling microparticles consisting of glycopyrronium bromide and a first part of the ICS in a ratio ranging from 80:20 to 70:30 by weight, wherein the volume diameter of said microparticles is no more than 15 micron;

(ii) mixing the coarse particles of a physiologically acceptable excipient, the salt of a fatty acid, a first part of said micronized particles of a physiologically acceptable excipient, the micronized particles of said LABA, the co-milled microparticles obtained in step (i), and the remaining part of the ICS in a vessel of a shaker mixer at a speed of rotation not lower than 16 r.p.m. for a time of not less than 60 minutes, to obtain a first mixture; and (iii) adding the remaining part of the micronized particles of a physiologically acceptable excipient to said first mixture, to obtain a second mixture, and mixing said second mixture at a speed of rotation not lower than 16 rpm for a time of at least 120 minutes to obtain a formulation.

In a preferred embodiment, the ICS is beclometasone dipropionate. In an even more preferred embodiment, the LABA is formoterol fumarate dihydrate and the additive is magnesium stearate.

DETAILED DESCRIPTION OF THE PREFERRED EMBODIMENTS

As used herein, the term "dry powder inhaler (DPI)" refers to a device that delivers medication to the lungs in the form of a dry powder DPIs can be divided into two basic types:

(i) single dose inhalers, for the administration of pre-subdivided single doses of the active compound; and
(ii) multidose dry powder inhalers (MDPIs), either with pre-subdivided single doses or pre-loaded with quantities of active ingredient sufficient for multiple doses; each dose is created by a metering unit within the inhaler.

On the basis of the required inspiratory flow rates (l/min) which in turn are strictly depending on their design and mechanical features, DPI's are also divided in:

(i) low-resistance devices (>90 l/min);
(ii) medium-resistance devices (about 60-90 l/min);
(iii) medium-high resistance devices (about 50-60 l/min); and
(iv) high-resistance devices (less than 30 l/min).

The reported classification is generated with respect to the flow rates required to produce a pressure drop of 4 KPa (KiloPascal) in accordance with the European Pharmacopoeia (Eur Ph), which is incorporated herein by reference in its entirety.

As used herein, the term "high-performing dry powder inhaler (DPI)" refers to a medium or high resistance breath-actuated multidose dry powder inhaler having a body with a mouthpiece and provided with a deagglomerator system for deagglomerating the powdered medicament comprising a vortex chamber (cyclone), wherein the air flow for the delivery of the medicament is not lower than 20 l/min, preferably in the range of 25 to 40 l/min.

The terms "muscarinic receptor antagonists", "anti-muscarinic drugs" and "anticholinergic drugs" can be used synonymously.

The term "glycopyrronium bromide" refers to the bromide salt of the compound (3S,2'R), (3R,2'S)-3-[(cyclopentylhydroxyphenylacetyl)oxy]-1,1-dimethylpyrrolidinium in approximately 1:1 racemic mixture, also known as glycopyrrolate.

The term "pharmaceutically acceptable salt of formoterol" refers to a salt of the compound 2'-hydroxy-5'-[(RS)-1-hydroxy-2 {[(RS)-p-methoxy-α-methylphenethyl]amino} ethyl] formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate.

The term "pharmaceutically acceptable salt" comprises inorganic and organic salts. Examples of organic salts may include formate, acetate, trifluoroacetate, propionate, butyrate, lactate, citrate, tartrate, malate, maleate, succinate, methanesulfonate, benzenesulfonate, xinofoate, pamoate, and benzoate. Examples of inorganic salts may include fluoride chloride, bromide, iodide, phosphate, nitrate and sulfate.

The term "physiologically acceptable excipient" refers to a pharmacologically-inert substance to be used as a carrier. In the context of the present invention, salts of fatty acids, that are also physiologically acceptable excipients, are defined as an additive.

The expression "shaker mixer" refers to a versatile mixer having a wide and adjustable range of speed of rotation and inversion cycles. In said mixers, the mixing container is gimbal-mounted. Two rotation axes are positioned perpendicularly each other, and are powered independently. The turning direction and rotational speed of both axes is subject to continual and independent change. The setting of these kind of mixing process parameters is able to guarantee a high value of mixing efficiency. A typical shaker mixer is commercially available as dyna-MIX™ (Willy A. Bachofen AG, Switzerland) or 3D.S mixer (Erhard Muhr GmbH, Germany).

The expression "tumbler mixer" refers to a mixer that works with different mixing times and mixing speeds and but with a typical movement characterized by the interaction of rotation, translation and inversion. A typical tumbler mixer is commercially available as Turbula™ (Willy A. Bachofen AG, Switzerland).

The expression instant or high-shear mixer refers to mixers wherein a rotor or impeller, together with a stationary component known as a stator is used either in a tank containing the powder to be mixed to create a shear.

Typical high-shear mixers are P 100 and P 300 (Diosna GmbH, Germany), Roto Mix (IMA, Italy), and Cyclomix™ (Hosokawa Micron Group Ltd, Japan). The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values: i) the median diameter d(0.5) which is the diameter where 50% of the distribution is above and 50% is below; ii) d(0.9), where 90% of the distribution is below this value; iii) d(0.1), where 10% of the distribution is below this value.

The span is the width of the distribution based on the 10%, 50% and 90% quantiles and is calculated according to the formula.

$$\text{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation the particle size of the active ingredients can be determined by scanning electron microscopy according to methods known to the skilled person in the art.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able of ensuring an accurate and reproducible delivery of the therapeutically effective dose.

Flow characteristics can be evaluated by different tests such as angle of repose, Carr index, Hausner ratio or flow rate through an orifice.

In the context of the present application the flow properties were tested by measuring the flow rate through an orifice according to the method described in the European Pharmacopeia (Eur. Ph.) 8.6, $8^{th}$ Edition, which is incorporated herein by reference in its entirety.

The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI) or Next Generation Impactor (NGI), according to procedures reported in common Pharmacopoeias, in particular in the European Pharmacopeia (Eur. Ph.) 8.4, $8^{th}$ Edition, which is incorporated herein by reference in its entirety. It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 micron.

Typically, a respirable fraction higher than 30% is considered an index of good aerosol performances.

A formulation is defined as "extrafine formulation" when, upon inhalation, the active ingredients are delivered with a fraction of particles having a particle size equal to or lower than 2.0 micron equal to or higher than 20%.

The term "mid FPF" refers to the fraction of delivered dose having a particle size comprised between 2.0 and 5.0.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al. J. Pharm. Pharmacol. 34,700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "chemically stable" refers to a formulation that, upon storage, meets the requirements of the EMEA Guideline CPMP/QWP/122/02 referring to 'Stability Testing of Existing Active Substances and Related Finished Products', which is incorporated herein by reference in its entirety.

The term "surface coating" refers to the covering of the surface of the carrier particles by forming a film of magnesium stearate around said particles. The thickness of the film has been estimated by X-ray photoelectron spectroscopy (XPS) to be approximately of less than 10 nm. The percentage of surface coating indicates the extent by which magnesium stearate coats the surface of all the carrier particles.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GINA), which is incorporated herein by reference in its entirety, "uncontrolled persistent asthma" is defined as a form characterized by daily symptoms, frequent exacerbations, frequent nocturnal asthma symptoms, limitation of physical activities, forced expiratory volume in one second ($FEV_1$) equal to or less than 80% predicted and with a variability higher than 30%.

According to the Global Initiative for Asthma (GINA) guidelines 2014, which is incorporated herein by reference in its entirety, "partially uncontrolled asthma" is defined as a form characterized by less than twice a week daily symptoms, less than twice a month, nocturnal asthma symptoms, and a forced expiratory volume in one second ($FEV_1$) higher than 80% with a variability comprised between 20 and 30%.

According to the Global initiative for chronic Obstructive Pulmonary Disease (GOLD) guidelines, which is incorporated herein by reference in its entirety, "severe COPD" is a form characterized by a ratio between $FEV_1$ and the Forced Vital Capacity (FVC) lower than 0.7 and $FEV_1$ between 30% and 50% predicted. The very severe form is further characterized by chronic respiratory failure.

"Therapeutically effective dose" means the quantity of active ingredients administered at one time by inhalation upon actuation of the inhaler. Said dose may be delivered in one or more actuations, preferably one actuation (shot) of the inhaler. The term "actuation" refers to the release of active ingredients from the device by a single activation (e.g. mechanical or breath).

The term "milling" refers to any mechanical process which applies sufficient energy to the particles that is capable of breaking coarse particles down to micronized particles (microparticles) of volume median diameter not more than 15 micron.

The terms "co-milling" and "co-micronization" are synonymous.

Wherein a numerical range is stated herein, the endpoints are included.

The present invention is directed to a process for the preparation of a dry powder formulation for use in a dry powder inhaler (DPI) comprising a carrier, and particles of glycopyrronium bromide, an inhaled corticosteroid (ICS) and a long-acting $β_2$-agonist (LABA) as active ingredients, wherein, as a first step, microparticles of glycopyrronium bromide and a first part of the ICS in a certain ratio are prepared by co-milling.

The LABA active ingredient, that may be present in form of pharmaceutically acceptable salts and/or solvate form thereof, may be selected from the group, which includes, but it is not limited to, formoterol, salmeterol, indacaterol, olodaterol, vilanterol, and the ultra-long-acting β2-adrenoreceptor agonist (uLABA) compound quoted with the code AZD3199.

The ICS, that may be anhydrous or present in form of hydrates, may be selected from the group which includes, but it is not limited to, beclomethasone dipropionate and its monohydrate form, budesonide, fluticasone propionate, fluticasone furoate, and mometasone furoate.

Preferably, the ICS is beclometasone dipropionate. More preferably, the LABA is formoterol fumarate dihydrate.

The microparticles of glycopyrronium bromide and ICS are obtained by co-milling.

Advantageously, the two active ingredients are pre-mixed before being subjected to co-milling in order to achieve a homogeneous mixture using apparatus and according to conditions known to the skilled person.

Advantageously, the ratio between glycopyrronium bromide and ICS, in the co-milling step, is 80:20 to 70:30 by weight, preferably of 75:25, by weight.

For example, if a single therapeutically effective dose of glycopyrronium bromide of 25 micrograms is requested, suitable amounts of the active ingredients will be used in such a way that the ratio between glycopyrronium bromide and ICS in said microparticles will vary between 25 micrograms to 5 micrograms and 25 micrograms to 15 micrograms.

If the ICS to be delivered is BDP at single therapeutically effective dose of 100 micrograms, a suitable amount will be then added as remaining part, corresponding to a single dose varying from 95 to 85 micrograms.

A wide range of milling devices and conditions are suitable. The selection of appropriate milling conditions, for example, intensity of milling and duration, to provide the required degree of force will be within the ability of the skilled person who will understand how to arrange those milling conditions such that the milling is capable of breaking down coarse particles. Ball milling is a preferred method. Alternatively, a high pressure homogenizer may be used in which a fluid containing the particles is forced through a valve at high pressure producing conditions of high shear and turbulence. Shear forces on the particles, impacts between the particles and machine surfaces or other particles and cavitation due to acceleration of the fluid may all contribute to the fracture of the particles. Such homogenizers may be more suitable than ball mills for use in large scale preparations of the above microparticles.

Suitable homogenizers include the EmulsiFlex high pressure homogenizer which is capable of pressure up to 4000 Bar, Niro Soavi high pressure homogenizers (capable of pressures up to 2000 Bar), and the Microfluidics Microfluidiser (maximum pressure 2750 Bar). The milling step may, alternatively, involve an agitator bead mill, for example, the DYNO-mill (Willy A. Bachofen AG, Switzerland) or the Netzsch high energy media mill. The Mechano-Fusion system (Hosokawa Micron Ltd) and the Hybridizer (Nara) are also suitable for use with the invention. Other possible milling devices include air jet mills, spiral jet mills, pin mills, hammer mills, knife mills and ultracentrifugal mills.

In a preferred embodiment of the present invention, a spiral jet mill may be utilized.

After the milling step, the volume diameter of the microparticles is no more than 15 microns, advantageously no more than 12 microns, more preferably no more than 10 microns. In a preferred embodiment, 90% by weight of said microparticles may have a diameter of less than 8 microns, preferably of less than 7 microns, the volume median diameter may be comprised between 1.0 and 3.0 microns, and no more than 10% of said microparticles may have a diameter lower than 0.6 microns.

The carrier A) is constituted of a) a fraction of coarse excipient particles and a fraction b) constituted of micronized excipients particles, and a salt of a fatty acid as an additive contributing to improve the respirable fraction.

The coarse excipient particles consist of 80 to 95 percent by weight of particles of a physiologically acceptable excipient having a mass median diameter equal to or higher than 175 microns.

Advantageously, all the coarse particles have a mass diameter in the range of 100 to 600 microns.

In certain embodiments of the invention, the mass diameter of said coarse particles might be 150 to 500 microns, preferably 200 to 400 microns.

In a preferred embodiment of the invention, the mass diameter of the coarse particles is 210 to 360 microns.

In general, the skilled person shall select the most appropriate size of the coarse excipient particles if commercially available or by sieving, using a proper classifier.

Advantageously, the coarse excipient particles may have a relatively highly fissured surface, that is, on which there are clefts and valleys and other recessed regions, referred to herein collectively as fissures. The "relatively highly fissured" coarse particles can be defined in terms of fissure index and/or rugosity coefficient as described in WO 01/78695, which is incorporated herein by reference in its entirety, in particular from page 15, line 28, to page 17, line 26, and WO 01/78693, which is incorporated herein by reference in its entirety, in particular from page 12, line 16, to page 14, line 11, and they could be characterized according to the description therein reported. Advantageously, the fissure index of said coarse particles is of at least 1.25, preferably of at least 1.5, more preferably of at least 2.0.

Said coarse particles may also be characterized in terms of tapped density or total intrusion volume measured as reported in WO 01/78695, which is incorporated herein by reference in its entirety.

The tapped density of said coarse particles may advantageously be less than 0.8 g/cm$^3$, preferably 0.8 to 0.5 g/cm$^3$. The total intrusion volume may be of at least 0.8 cm$^3$, preferably at least 0.9 cm$^3$.

The fraction of micronized particles b) comprises of 19.6 to 4.9 percent by weight of particles of a physiologically acceptable excipient wherein at least 90% of said particles have a volume diameter lower than 15 microns, preferably lower than 12 microns. Advantageously, the volume median diameter of said particles is 3 to 7 microns, preferably 4 to 6 microns, and no more than 10% of said particles have a diameter lower than 2.5 microns, preferably lower than 2.0 microns.

Advantageously, the fine and coarse excipient particles may consist of any pharmacologically inert, physiologically acceptable material or combination thereof; preferred excipients are those made of crystalline sugars, in particular lactose; the most preferred are those made of α-lactose monohydrate.

Preferably, the coarse excipient particles and the fine excipient particles both consist of α-lactose monohydrate.

Said fraction b) further comprises 0.1 to 0.4 percent by weight of a salt of a fatty acid such as lauric acid, palmitic acid, stearic acid, behenic acid, or derivatives (such as esters and salts) thereof. Specific examples of such salts of fatty acids are: magnesium stearate; sodium stearyl fumarate; sodium stearyl lactylate; sodium lauryl sulfate, magnesium lauryl sulfate.

The preferred salt of fatty acid is magnesium stearate.

Advantageously, if it is used as the additive, magnesium stearate coats the surface of the coarse and micronized excipient particles a) and b) in such a way that the extent of the surface coating is at least of 5%, more advantageously, higher than 10%.

The extent to which the magnesium stearate coats the surface of the excipient particles may be determined according to the methods disclosed in WO 2015/004243, which is incorporated herein by reference in its entirety, in particular from page 12, line 16, to page 14, line 11.

More advantageously, the ratio among the fraction of coarse particles a), the micronized excipient particles, and magnesium stearate may be 85:14.7:0.3 to 90:9.8:0.2 by weight, preferably 90:9.8:0.2 by weight.

Advantageously, the whole amount of coarse particles a) are mixed with the whole amount of magnesium stearate and with a first part of the micronized excipient particles.

Advantageously, said first part is from 40% to 60%, more advantageously from 45 to 55%, preferably 50%, based on the total weight of all micronized excipient particles.

The mixing may be performed in any suitable mixer, e.g. tumbler mixers such as Turbula™ for at least 5 minutes, preferably for at least 30 minutes, more preferably for at least two hours.

In a general way, the skilled person shall adjust the time of mixing and the speed of rotation of the mixer to obtain a homogenous mixture.

When spheronized carrier particles are desired to obtain hard-pellets according to the definition reported above, the step of mixing shall be typically carried out for at least four hours.

Since the mixing step does not alter the particle size, the person skilled in the art shall select the suitable size of the coarse excipient particles, that of the micronized excipient particles as well as that of magnesium stearate, either by sieving, by using a classifier to achieve the desired particle size distribution, being sure that final particle size of blend will correspond to the staring one.

Materials of the desired particle size distribution are also commercially available.

In one embodiment of the invention, the carrier (A) consisting of the coarse excipient particles (a), 50% of the micronized excipient particles, and the particles of magnesium stearate may be prepared by mixing in a Turbula™ mixer or in a dyna-MIX mixer at a rotation speed of 11 to 45 rpm, preferably 16 to 32 rpm, for a period of at least 30 minutes, preferably comprised between 60 and 300 minutes.

In step (ii), the carrier (A), the micronized particles of the ICS, the LABA and the anti-muscarinic drug are poured in the vessel of a shaker mixer having a wide and adjustable range of speed of rotation and inversion cycles.

It has indeed been found that said type of mixers are particularly suitable due to their versatility. In fact, with said mixers, frequent changes in the revolution cycles can be set in order to continuously change the powder flow inside the mixing and create powder flow patterns within the drum and to increase mixing efficacy.

In a preferred embodiment of the invention, the dyna-MIX™ mixer is utilized.

The blend of step (ii) is mixed at a speed of rotation of at least 16 r.p.m., preferably between 20 and 28 r.p.m, for a time of not less than 60 minutes, preferably comprised between 60 and 120 minutes.

In step (iii), the remaining part of the micronized physiologically acceptable excipient is added and mixed at a speed of rotation not lower than 16 rpm, preferably from 16 to 32 r.p.m., for a time of at least 120 minutes, preferably from 120 to 180 minutes.

Optionally, the resulting mixture is sieved through a sieve. The skilled person shall select the mesh size of the sieve depending on the particle size of the coarse particles.

The blend of step (iii) may be finally (iv) mixed in any suitable mixer to achieve a homogeneous distribution of the active ingredients.

The skilled person shall select the suitable mixer and adjust the time of mixing and the speed of rotation of the mixer to obtain a homogenous mixture.

Advantageously, each active ingredient is present in the formulation of the invention in a crystalline form, more preferably with a crystallinity degree higher than 95%, even more preferably higher than 98%, as determined according to known methods.

Since the powder formulation obtained with the process of the invention should be administered to the lungs by inhalation, at least 99% of said particles [d(v,0.99)] shall have a volume diameter equal to or lower than 10 microns, and substantially all the particles have a volume diameter comprised between 8 and 0.4 microns.

Advantageously, in order to better achieve the distal tract of the respiratory tree, 90% of the micronized particles of the ICS and LABA active ingredients shall have a volume diameter lower than 6.0 microns, preferably equal to or lower than 5.0 microns, the volume median diameter shall be 1.2 to 2.5 microns, preferably 1.3 to 2.2 microns, and no more than 10% of said shall have a diameter lower than 0.6 microns, preferably equal to or lower than 0.7 microns, more preferably equal to or lower than 0.8 microns.

It follows that the width of the particle size distribution of the particles of the ISC and LABA active ingredients, expressed as a span, shall be advantageously 1.0 to 4.0, more advantageously 1.2 to 3.5. According the Chew et al J Pharm Pharmaceut Sci 2002, 5, 162-168, which is incorporated herein by reference in its entirety, the span corresponds to $$[d(v,0.9)-d(v,0.1)]/d(v,0.5).$$

The size of the particles active is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

In a preferred embodiment, the Helos Aspiros instrument (Sympatec GmbH, Clausthal-Zellerfeld, Germany) is utilized. Typical conditions are: Fraunhofer FREE or Fraunhofer HRLD algorithm, R1 (0.1/0.18-35 micron) or R2 (0.25/0.45-87.5 micron) lens, 1 bar pressure.

As for the particle size determination, a CV of ±30% for the d(v0,1) and a CV of ±20% for the d(v0,5), d(v0,9) and d(v0,99) are considered within the experimental error.

The micronized LABA and ICS active ingredients utilized in the formulation may be prepared by processing in a suitable mill according to known methods.

In one embodiment of the invention, they can be prepared by grinding using a conventional fluid energy mill such as commercially available jet mill micronizers having grinding chambers of different diameters.

Depending on the type of the apparatus and size of the batch, the person skilled in the art shall suitably adjust the milling parameters such as the operating pressure, the feeding rate and other operating conditions to achieve the desired particle size. Preferably all the micronized active ingredients are obtained without using any additive during the micronization process.

The powder formulation comprising micronized particles of glycopyrronium bromide, beclometasone dipropionate, and formoterol fumarate dihydrate as active ingredients, obtainable according to process of the invention, is physically and chemically stable, freely flowable and exhibits a good homogeneity of the active ingredients.

The ratio between the carrier particles and the active ingredients will depend on the type of inhaler used and the required dose.

The powder formulations obtained by the process of the invention may be suitable for delivering a therapeutic amount of all active ingredients in one or more actuations (shots or puffs) of the inhaler.

Advantageously, said formulations shall be suitable for delivering a therapeutically effective dose of all three active ingredients of 50 to 600 µg, preferably 100 to 500 µg.

For example, the formulations will be suitable for delivering 3 to 15 µg of formoterol (as fumarate dihydrate) per actuation, advantageously 5.5 to 6.5 µg or 10 to 13 µg per actuation, preferably 6 or 12 µg per actuation; 25-250 µg of beclometasone dipropionate (BDP) per actuation, advantageously 40 to 60 µg per actuation, or 80 to 120 µg per actuation, or 160 to 240 µg per actuation; and 5 to 65 µg of glycopyrronium (as bromide), advantageously 5 to 15 µg per actuation, or 20 to 30 µg per actuation, preferably 12.5 µg or 25 µg.

In a particular embodiment, the formulation is suitable for delivering 6 µg of formoterol (as fumarate dihydrate) per actuation, 100 µg of beclometasone dipropionate per actuation, and 12.5 µg of glycopyrronium (as bromide) per actuation.

In another embodiment, the formulation is suitable for delivering 12 µg of formoterol (as fumarate dihydrate) per actuation, 200 µg of beclometasone dipropionate per actuation, and 25 µg of glycopyrronium (as bromide) per actuation.

Said powder formulation may be utilized with any dry powder inhaler.

Dry powder inhaler (DPIs) can be divided into two basic types:

(i) single dose inhalers, for the administration of single subdivided doses of the active compound; each single dose is usually filled in a capsule; and (ii) multidose inhalers pre-loaded with quantities of active principles sufficient for longer treatment cycles.

The dry powder formulations may be utilized with either multidose DPIs comprising a reservoir from which individual therapeutic dosages can be withdrawn on demand through actuation of the device, or with single dose inhalers.

Typical multidose devices that may be used are, for instance, Diskus™ of GlaxoSmithKline, Turbohaler™ of AstraZeneca, Twisthaler™ of Schering, Clickhaler™ of Innovata, Spiromax™ of Teva, Novolizer™ of Meda, and Genuair™ of Almirall.

Examples of marketed single dose devices include Rotohaler™ of GlaxoSmithKline, Handihaler™ of Boehringer Ingelheim, and Breezehaler™ of Novartis.

Preferably, the powder formulation obtained with the process of the present invention is filled in a high-performing multidose DPI selected from the group consisting of the multidose dry powder inhaler disclosed in WO 2004/012801, which is incorporated herein by reference in its entirety, in particular from page 1, first line, to page 39, last line, and its variant disclosed in WO2016/000983, which is incorporated herein by reference in its entirety, in particular from page 1, line 5, to page 15, line 34.

Other suitable high-performing multidose DPI are Novolizer™, and Genuair™.

To protect the DPIs from ingress of moisture into the formulation, it may be desirable to overwrap the device in a flexible package capable of resisting moisture ingress such as that disclosed in EP 1 760 008, which is incorporated herein by reference in its entirety, in particular from page 2, paragraph [0009] to page 9, paragraph [102].

Administration of the formulation prepared according to the process of the invention is indicated for the prevention and/or treatment of chronic obstructive pulmonary disease (COPD) and asthma of all types and severity.

The formulation prepared according to the process of the present invention is also indicated for the prevention and/or treatment of further respiratory disorders characterized by obstruction of the peripheral airways as a result of inflammation and presence of mucus such as chronic obstructive bronchiolitis.

In certain embodiments, said formulation is particularly suitable for the prevention and/or treatment of severe and/or very severe forms COPD, and in particular for the maintenance treatment of COPD patients with symptoms, airflow limitation and history of exacerbations.

Furthermore, it might be suitable for the prevention and/or treatment of persistent asthma and asthma in patients not controlled with medium or high doses of ICS in combination with LABAs.

Other features of the invention will become apparent in the course of the following descriptions of exemplary embodiments which are given for illustration of the invention and are not intended to be limiting thereof.

EXAMPLES

Example 1. Preparation of the Carrier

Micronized alpha-lactose monohydrate (DFE Pharma, Germany) having the following particle size was used: d(v0.1)=1.5 micron; d(v0.5)=3.6 micron; and d(v0.9)=7.5 micron was utilized. About 1694 g of said micronized alpha-lactose monohydrate, about 69.2 g of magnesium stearate (Peter Greven, Germany) and about 31.13 kg of fissured coarse particles of α-lactose monohydrate having a mass diameter of 212-355 microns (in the ratio 90:10 by weight (coarse lactose to micronized lactose+MgSt) were fed into the vessel of a Turbula™ mixer (Willy A. Bachofen AG, Germany) and mixed. The mixing was carried out for 240 minutes at a speed of rotation of 16 r.p.m.

Example 2. Preparation and Characterization of the Co-Milled Microparticles

Rac-glycopyrronium bromide (GB) and beclometasone dipropionate (BDP) commercially available were utilized. The crystalline active ingredients were pre-mixed in a Turbula™ mixer in a ratio of 75:25 by weight, in order to achieve a homogeneous mixture. The crystalline mixture was then micronized using a spiral jet-mill MC50 (Micro-Macinazione, Lugano, Switzerland) applying the following parameters:

Powder feeding speed: 0.875 Kg/h;
Milling volumetric flow rate: 16 nm$^3$/h; and
Feeding volumetric flow rate: 8 nm$^3$/h.

For comparative purposes, crystalline rac-GB alone was micronized with the following process parameters:

Powder feeding speed: 0.875 Kg/h;
Milling volumetric flow rate: 16 nm$^3$/h; and
Feeding volumetric flow rate: 8 nm$^3$/h.

Co-micronized microparticles and reference micronized glycopyrronium bromide were exposed to the following conditions:

Thin layer (~0.5 cm) in open tray for 3 days at 30° C./65% relative humidity (RH);

Thin layer (~0.5 cm) in open tray for 4 hours at 25° C./90% RH.

The following analyses were performed:

(i) particle size distribution (PSD) in terms of d(v0.1), d(v0.5) and d(v0.9) by Malvern analysis, (ii) Specific Surface Area (SSA) by Brunauer-Emmett-Teller (BET) nitrogen adsorption method according to a known procedure, and (iii) recrystallization of water using a Dynamic Vapour Sorption (DVS) instrument (Mettler Toledo GmbH, Switzerland).

The analytical results are summarized in Table 1.

TABLE 1

|  |  | SSA (m$^2$/g) | PSD | | | Re-crystallization water (% w/w) |
|---|---|---|---|---|---|---|
|  |  |  | d(v0.1) (μm) | d(v0.5) (μm) | D(v0.9) (μm) |  |
| Co-micronized GB/BDP | Initial | 5.8 | 0.61 | 2.07 | 5.71 | 0.19 |
|  | Open thin layer 4 hours at 25° C./90% RH | Not measured | 0.68 | 2.42 | 5.99 | Not measured |
|  | Open thin layer 3 days at 30° C./65% RH | 4.07 | 0.62 | 2.30 | 5.97 | 0.10 |
| Micronized GB | Initial | 7.31 | 0.60 | 1.54 | 3.95 | 0.12 |
|  | Open thin layer 4 hours at 25° C./90% RH | Not measured | 2.74 | 156 | 1657 | Not measured |
|  | Open thin layer 3 days at 30° C./65% RH | 1.85 | 1.00 | 3.91 | 7.59 | 0.02% |

As it can be appreciated, co-micronized microparticles show no significant variation in particle size distribution and in the other related parameters upon exposure to both conditions, while micronized GB alone experienced a significant increase of the particle size, in particular at 25° C. and 90% RH, indicating that a significant agglomeration occurred.

Example 3. Preparation of the Dry Powder Formulation

Microparticles as obtained in Example 2 were used. Micronized formoterol fumarate dihydrate (FF) having the following particle size was used: d(v0.1)=0.9 micron; d(v0.5)=2.3 micron; and d(v0.9)=4.2 micron. Beclometasone dipropionate (BDP) having the following particle size was used: d(v0.1)=0.7 micron; d(v0.5)=1.5 micron; and d(v0.9)=2.8 micron.

The carrier as obtained in Example 1 was mixed in a dyna-MIX™ mixer with formoterol fumarate dihydrate, the microparticles, and the remaining part of BDP in order to have a final therapeutic effective dose of 100 micrograms per actuation of the inhaler. The mixer was operated at a speed of rotation of 24 and 28 r.p.m. alternatively for the two rotation axes for a time of 80 minutes. Then 1694 g of micronized alpha-lactose monohydrate were added and mixed at a speed of rotation between 16 and 32 r.p.m. alternatively for the two rotation axes for a time of 150 minutes.

The resulting mixture was poured into a sieving machine available from Frewitt (Fribourg, Switzerland) equipped with a 600 micron mesh size sieve. Upon sieving, the blend was finally mixed in a in the Dynamix mixer for 60 minutes at a rotation speed of 24 and 32 r.p.m alternately to achieve an homogeneous distribution of the active ingredients.

The ratio of the active ingredients to 10 mg of the carrier is 6 micrograms (μg) of FF dihydrate (theoretical delivered dose 4.5 μg), 100 micrograms (μg) of BDP, and 12.5 micrograms (μg) of glycopyrronium bromide (theoretical delivered dose 10.0 μg).

The powder formulation was characterized in terms of the uniformity of distribution of the active ingredients and aerosol performances after loading it in the multidose dry powder inhaler disclosed in WO 2004/012801, which is incorporated herein by reference in its entirety. The uniformity of distribution of the active ingredients was evaluated by withdrawing 10 samples from different parts of the blend and evaluated by HPLC. The results (mean value±RSD) are reported in Table 2.

The evaluation of the aerosol performance was carried out using the Next Generation Impactor (NGI) according to the conditions reported in the European Pharmacopeia 8.5th Ed 2015, which is incorporated herein by reference in its entirety, par 2.9.18, pages 309-320. After aerosolization of 3 doses from the inhaler device, the NGI apparatus was disassembled and the amounts of drug deposited in the stages were recovered by washing with a solvent mixture and then quantified by High-Performance Liquid Chromatography (HPLC).

The following parameters, were calculated: (i) the delivered dose which is the amount of drug delivered from the device recovered in the all parts of impactor; (ii) the fine particle mass (FPM) which is the amount of delivered dose having a particle size equal to or lower than 5.0 microns; (iii) the extrafine FPM which is the amount of delivered dose having a particle size equal to or lower than 2.0 microns and/or equal to or lower than 1.0 micron; (iv) the mid FPM which is the amount of delivered dose having a particle size comprised between 2.0 and 5.0 microns; (v) the fine particle fraction (FPF) which is the ratio between the fine particle mass and the delivered dose; and (vi) the MMAD. The results (mean value±S.D) are reported in Table 2.

TABLE 2

| | Active ingredient |
|---|---|
| | FF |
| Uniformity of distribution | 100.5 (±1.5) |
| Delivered Dose [μg] | 5.1 |
| Fine Particle Mass [μg] | 2.9 |
| Fine Particle Fraction [%] | 54.8 |
| Mid Fine Particle Mass [μg] | 1.24 |
| Extrafine Particle Mass <2 μm [μg] | 1.7 |
| Extrafine Particle Mass <1 μm [μg] | 0.6 |
| Mid Fine particle Fraction [%] | 24.1 |
| Extrafine Particle Fraction <2 μm [%] | 32.5 |
| Extrafine Particle Fraction <1 μm [%] | 11.7 |
| MMAD [μm] | 1.9 |
| | GB |
| Uniformity of distribution | 101.4 (±1.6) |
| Delivered Dose [μg] | 11.1 |
| Fine Particle Mass [μg] | 5.4 |
| Fine Particle Fraction [%] | 48.1 |
| Mid Fine Particle Mass [μg] | 2.4 |
| Extrafine Particle Mass <2 μm [μg] | 2.9 |
| Extrafine Particle Mass <1 μm [μg] | 1.1 |
| Mid Fine particle Fraction [%] | 21.6 |
| Extrafine Particle Fraction <2 μm [%] | 26.4 |
| Extrafine Particle Fraction <1 μm [%] | 9.8 |
| MMAD [μm] | 1.9 |
| | BDP |
| Uniformity of distribution | 100.5 (±1.8) |
| Delivered Dose [μg] | 88.5 |
| Fine Particle Mass [μg] | 43.6 |
| Fine Particle Fraction [%] | 49.3 |
| Mid Fine Particle Mass [μg] | 15.2 |
| Extrafine Particle Mass <2 μm [μg] | 28.5 |
| Extrafine Particle Mass <1 μm [μg] | 12.4 |
| Mid Fine particle Fraction [%] | 17.1 |
| Extrafine Particle Fraction <2 μm [%] | 32.1 |
| Extrafine Particle Fraction <1 μm [%] | 13.9 |
| MMAD [μm] | 1.6 |

Example 5. Determination of the Caking Tendency

It is known that moisture increases the cohesive strength between glycopyrronium bromide (GB) particles to the extent that it can cause caking. Additionally, phase transformations (i.e. crystallization of the amorphous fraction present in the micronized GB particles) triggered by ambient relative humidity (RH) above 45% can result in fusing/sintering of the GB particles causing lumps and severe caking.

A test has been performed to determine the agglomeration/caking tendency of the co-milled microparticles of the invention versus reference micronized GB. The materials were prepared as reported in Example 2. The samples were tested at the following ambient conditions:
30% RH, 22° C.;
60% RH, 32° C.;
Transition from 30% RH, 32° C. to 60% RH, 32° C.

The experiments were performed using a Dynamic Vapour Sorption (DVS) Analyzer from Surface Measurement Systems (London, UK). The co-milled microparticles of the invention are significantly less likely to cake compared to the reference material.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing a powder formulation for inhalation for use in a dry powder inhaler, said powder comprising:
   (A) a carrier, comprising:
     (a) 80 to 95 percent by weight, based on the total weight of said carrier, of coarse particles of a physiologically acceptable excipient having a mean particle size of at least 175 microns;
     (b) 19.6 to 4.9 percent by weight, based on the total weight of said carrier, of micronized particles of a physiologically acceptable excipient; and
     (c) 0.1 to 0.4 percent by weight, based on the total weight of said carrier, of a salt of a fatty acid; and
   (B) micronized particles of glycopyrronium bromide, micronized particles of a long-acting $\beta_2$-agonist (LABA), and micronized particles of an inhaled corticosteroid (ICS), as active ingredients,
   said process comprising:
   (i) preparing, by co-milling, microparticles comprising glycopyrronium bromide and a first part of said ICS in a ratio of 80:20 to 70:30 by weight, wherein the volume diameter of said microparticles is no more than 15 micron;
   (ii) mixing said coarse particles of a physiologically acceptable excipient (a), said salt of a fatty acid (c), a first part of said micronized particles of a physiologically acceptable excipient (b), said micronized particles of said LABA, said co-milled microparticles obtained in step (i), and the remaining part of said ICS in a vessel of a shaker mixer at a speed of rotation not lower than 16 r.p.m. for a time of not less than 60 minutes, to obtain a first mixture; and
   (iii) adding the remaining part of said micronized particles of a physiologically acceptable excipient to said first mixture, to obtain a second mixture, and mixing said second mixture at a speed of rotation not lower than 16 rpm for a time of at least 120 minutes to obtain a formulation.

2. A process according to claim 1, further comprising: (iv) further mixing said formulation obtained in (iii) to achieve a homogeneous distribution of said active ingredients.

3. A process according to claim 1, wherein said first part of said micronized particles of a physiologically acceptable excipient is 40% to 60%, based on the total weight of all of said micronized particles of a physiologically acceptable excipient.

4. A process according to claim 1, wherein said ICS is selected from the group consisting of beclomethasone dipropionate and its monohydrate form, budesonide, fluticasone propionate, fluticasone furoate, and mometasone furoate.

5. A process according to claim 1, wherein said LABA is selected from the group consisting of formoterol, salmeterol, indacaterol, olodaterol, and vilanterol.

6. A process according to claim 1, wherein said ICS is beclometasone dipropionate, and said LABA is formoterol fumarate dihydrate.

7. A process according to claim 1, wherein said salt of a fatty acid is selected from the group consisting of magnesium stearate, sodium stearyl fumarate, sodium stearyl lactylate, sodium lauryl sulfate, and magnesium lauryl sulfate.

8. A process according to claim 7, wherein said salt of the fatty acid is magnesium stearate.

9. A process according to claim 1, wherein said mixing (ii) is performed at a speed of rotation of 20 to 28 r.p.m for a time of 60 to 120 minutes.

10. A process according to claim 1, wherein step (iii) said mixing is performed at a speed of rotation of 16 to 32 r.p.m for a time of 120 to 180 minutes.

11. A process according to claim 1, wherein said physiologically acceptable excipient in said coarse particles of said physiologically acceptable excipient is alpha-lactose monohydrate.

12. A process according to claim 1, wherein said physiologically acceptable excipient in said micronized particles said physiologically acceptable excipient is alpha-lactose monohydrate.

13. A process according to claim 1, wherein said physiologically acceptable excipient in said coarse particles said physiologically acceptable excipient is alpha-lactose monohydrate and said physiologically acceptable excipient in said micronized particles said physiologically acceptable excipient is alpha-lactose.

14. A process according to claim 1, wherein said coarse particles of said physiologically acceptable excipient have a mass diameter of 210 to 360 µM.

15. A powder formulation, which is prepared by a process according to claim 1.

16. A dry powder inhaler, containing a powder formulation prepared by a process according to claim 1.

* * * * *